United States Patent
Mazumder et al.

(10) Patent No.: US 11,462,331 B2
(45) Date of Patent: Oct. 4, 2022

(54) METHOD AND SYSTEM FOR PRESSURE AUTOREGULATION BASED SYNTHESIZING OF PHOTOPLETHYSMOGRAM SIGNAL

(71) Applicant: Tata Consultancy Services Limited, Mumbai (IN)

(72) Inventors: Oishee Mazumder, Kolkata (IN); Dibyendu Roy, Kolkata (IN); Sakyajit Bhattacharya, Kolkata (IN); Aniruddha Sinha, Kolkata (IN); Arpan Pal, Kolkata (IN)

(73) Assignee: TATA CONSULTANCY SERVICES LIMITED, Mumbai (IN)

(*) Notice: Subject to any disclaimer, the term of this patent is extended or adjusted under 35 U.S.C. 154(b) by 462 days.

(21) Appl. No.: 16/809,964

(22) Filed: Mar. 5, 2020

(65) Prior Publication Data

US 2021/0027895 A1 Jan. 28, 2021

(30) Foreign Application Priority Data

Jul. 22, 2019 (IN) .............................. 201921029536

(51) Int. Cl.
*G16H 50/50* (2018.01)
*G06F 30/28* (2020.01)
(Continued)

(52) U.S. Cl.
CPC ......... *G16H 50/50* (2018.01); *A61B 5/02007* (2013.01); *A61B 5/02255* (2013.01);
(Continued)

(58) Field of Classification Search
CPC .......................... G16H 50/50; A61B 5/02007; A61B 5/02255; A61B 5/02416; A61B 5/7278; G06F 30/28
(Continued)

(56) References Cited

U.S. PATENT DOCUMENTS 9,881,523 B2  1/2018 Sweeney
2003/0179888 A1  9/2003 Burnett et al.
(Continued)

FOREIGN PATENT DOCUMENTS

CA  3097663  * 10/2019  .............. A61B 5/02
EP  3770921  * 1/2021  ............. G16H 50/50
(Continued)

OTHER PUBLICATIONS

Paradkar; Coronary Artery Disease Detection Using Photoplethsmography; 2017; IEEE; pp. 100-103.*
(Continued)

*Primary Examiner* — Jerome Grant, II
(74) *Attorney, Agent, or Firm* — Finnegan, Henderson, Farabow, Garrett & Dunner LLP

(57) ABSTRACT

The disclosure relates to digital twin of cardiovascular system called as cardiovascular model to generate synthetic Photoplethysmogram (PPG) signal pertaining to disease conditions. The conventional methods are stochastic model capable of generating statistically equivalent PPG signals by utilizing shape parameterization and a nonstationary model of PPG signal time evolution. But these technique generates only patient specific PPG signatures and do not correlate with pathophysiological changes. Further, these techniques like most synthetic data generation techniques lack interpretability. The cardiovascular model of the present disclosure is configured to generate the plurality of synthetic PPG signals corresponding to the plurality of disease conditions. The plurality of synthetic PPG signals can be used to tune Machine Learning algorithms. Further, the plurality of synthetic PPG signals can be utilized to understand, analyze and classify cardiovascular disease progression.

19 Claims, 9 Drawing Sheets

(51) Int. Cl.
  *A61B 5/02* (2006.01)
  *A61B 5/0225* (2006.01)
  *A61B 5/024* (2006.01)
  *A61B 5/00* (2006.01)
(52) U.S. Cl.
  CPC ........ *A61B 5/02416* (2013.01); *A61B 5/7278* (2013.01); *G06F 30/28* (2020.01)
(58) Field of Classification Search
  USPC .......................................................... 703/11
  See application file for complete search history.

(56) References Cited

U.S. PATENT DOCUMENTS

2020/0029836 A1* 1/2020 Corradini ................. A61B 5/01
2021/0193311 A1* 6/2021 Addison ................ G16H 40/40

FOREIGN PATENT DOCUMENTS

RU       2236816     *  9/2004   ............... A61B 5/26
WO   WO2021259958   * 12/2021   ............... A61B 5/21

OTHER PUBLICATIONS

Gupta; Dynamic Large Artery Stiffness Index for Cuffless Blood Pressure Estimation; 2022; IEEE ; vol. 6, No. 3; 4 pgs.*
V, V. et al. "Synthetic ECG and PPG Signal Generation Using Pulse Shaping Technique," *2015 Annual IEEE India Conference (INDICON)*, Dec. 17-20, 2015, New Delhi, India; pp. 1-6.
Mahdi, A. et al. (2017). "A model for generating synthetic arterial blood pressure," *Physiological Measurement*, vol. 38; pp. 477-488.

* cited by examiner

METHOD AND SYSTEM FOR PRESSURE AUTOREGULATION BASED SYNTHESIZING OF PHOTOPLETHYSMOGRAM SIGNAL

PRIORITY CLAIM

This U.S. patent application claims priority under 35 U.S.C. § 119 to: India Application No. 201921029536, filed on Jul. 22, 2019. The entire contents of the aforementioned application are incorporated herein by reference.

TECHNICAL FIELD

The disclosure herein generally relates to the field of health monitoring, and, more particular, to a method and system for pressure autoregulation based synthesizing of Photoplethysmogram (PPG) signal.

BACKGROUND

Cardiovascular disease has been ranked as a main cause of death worldwide by World Health Organization and early monitoring of such diseases are a major focus of the medical and scientific research community. A crucial part in monitoring cardiovascular disease is processing and decoding functional information available in cardiac physiological signals like electrocardiogram (ECG), Photoplythesmogram (PPG) and Phonocardiogram (PCG). PPG is a noninvasive and hassle free method for capturing Digital Volume Pulse (DVP) signals. The DVP signals are obtained from peripheral pulse sites such as the ear lobe, fingertip and toe. Further, PPG waveform provides useful information related to general conditions of major conduit vessels like aorta and other distal peripheral arteries. Hence synthetic generation of PPG signal is a vital requirement to analyze cardiovascular disease conditions.

Conventional methods provides different techniques to regenerate ECG, PCG and PPG signals mathematically, for example, stochastic modeling. In stochastic modelling, subject specific atlases of PPG signals were generated along with a set of parameters. The set of parameters provides regeneration of statistically equivalent PPG signals by utilizing shape parameterization and a nonstationary model of PPG signal time evolution. However, these technique generates only subject specific PPG signatures and do not correlate with pathophysiological changes. Further, these techniques lack interpretability.

SUMMARY

Embodiments of the present disclosure present technological improvements as solutions to one or more of the above-mentioned technical problems recognized by the inventors in conventional systems. For example, in one embodiment, a method for pressure autoregulation based synthesizing of PPG signal is provided. The method includes receiving, receiving a plurality of systolic phase parameters and a plurality of diastolic phase parameters associated with the cardiovascular model. Further, the method includes computing a systolic phase of a PPG signal based on the plurality of systolic phase parameters by utilizing a systolic contractility f unction comprises a plurality of systolic time constants, a systolic duration and a cardiac cycle duration, Further, the method includes computing a diastolic phase of the PPG signal based on a plurality of diastolic phase parameters by utilizing a diastole contractility function and the baroreflex control, wherein the diastolic contractility function comprises a plurality of diastolic time constants, a diastolic duration and the cardiac cycle duration. Further, the method includes generating a synthetic PPG signal based on the computed systolic phase and the diastolic phase of the PPG signal, wherein the synthetic PPG signal is associated with a plurality of the synthetic PPG signal parameters. Further, the method includes simultaneously fetching, a plurality of predetermined morphological features associated with a PPG signal from a database. Furthermore, the method includes optimizing the plurality of synthetic PPG signal parameters to obtain a plurality of optimized parameters by utilizing the plurality of predetermined morphological features. Finally, the method includes generating the plurality of synthetic PPG signals corresponding to the plurality of disease conditions by varying the plurality of parameters, wherein the plurality of parameters includes the plurality of optimized parameters and a plurality of cardiovascular model parameters.

In another aspect, a system for pressure autoregulation based synthesizing of PPG signal is provided. The system includes a computing device wherein the computing device includes, at least one memory comprising programmed instructions, at least one hardware processor operatively coupled to the at least one memory, wherein the at least one hardware processor is capable of executing the programmed instructions stored in the at least one memories and a cardiovascular unit, wherein the cardiovascular unit is configured to receive a plurality of systolic phase parameters and a plurality of diastolic phase parameters associated with the cardiovascular model. Further, the cardiovascular unit is configured to compute a systolic phase of a PPG signal based on the plurality of systolic phase parameters by utilizing a systolic contractility function and a baroreflex control, wherein the systolic contractility function includes a plurality of systolic time constants, a systolic duration and a cardiac cycle duration. Further, the cardiovascular unit is configured to compute a diastolic phase of the PPG signal based on a plurality of diastolic phase parameters by utilizing a diastole contractility function and the baroreflex control, wherein the diastolic contractility function includes a plurality of diastolic time constants, a diastolic duration and the cardiac cycle duration. Further, the cardiovascular unit is configured to generate a synthetic PPG signal based on the computed systolic phase and the diastolic phase of the PPG signal, wherein the synthetic PPG signal is associated with a plurality of the synthetic PPG signal parameters. Further, the cardiovascular unit is configured to simultaneously fetch a plurality of predetermined morphological features associated with a PPG signal from a database. Furthermore, the cardiovascular unit is configured to optimize the plurality of synthetic PPG signal parameters to obtain a plurality of optimized parameters by utilizing the plurality of predetermined morphological features. Finally, the cardiovascular unit is configured to generate the plurality of synthetic PPG signals corresponding to the plurality of disease conditions by varying the plurality of parameters, wherein the plurality of parameters includes the plurality of optimized parameters and a plurality of cardiovascular model parameters.

In yet another aspect, a computer program product comprising a non-transitory computer-readable medium having the cardiovascular unit is configured to embodied therein a computer program for method and system for pressure autoregulation based synthesizing of PPG signal is provided. The computer readable program, when executed on a computing device, causes the computing device to receive a plurality of systolic phase parameters and a plurality of diastolic phase parameters associated with the cardiovascular model. Further, the computer readable program, when executed on a computing device, causes the computing device to compute a systolic phase of a PPG signal based on the plurality of systolic phase parameters by utilizing a systolic contractility function and a baroreflex control, wherein the systolic contractility function includes a plurality of systolic time constants, a systolic duration and a cardiac cycle duration. Further, the computer readable program, when executed on a computing device, causes the computing device to compute a diastolic phase of the PPG signal based on a plurality of diastolic phase parameters by utilizing a diastole contractility function and the baroreflex control, wherein the diastolic contractility function includes a plurality of diastolic time constants, a diastolic duration and the cardiac cycle duration. Further, the computer readable program, when executed on a computing device, causes the computing device to generate a synthetic PPG signal based on the computed systolic phase and the diastolic phase of the PPG signal, wherein the synthetic PPG signal is associated with a plurality of the synthetic PPG signal parameters. Further, the computer readable program, when executed on a computing device, causes the computing device to simultaneously fetch a plurality of predetermined morphological features associated with a PPG signal from a database. Furthermore, the computer readable program, when executed on a computing device, causes the computing device to optimizing the plurality of synthetic PPG signal parameters to obtain a plurality of optimized parameters by utilizing the plurality of predetermined morphological features. Finally, the computer readable program, when executed on a computing device, causes the computing device to generate the plurality of synthetic PPG signals corresponding to the plurality of disease conditions by varying the plurality of parameters, wherein the plurality of parameters includes the plurality of optimized parameters and a plurality of cardiovascular model parameters.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
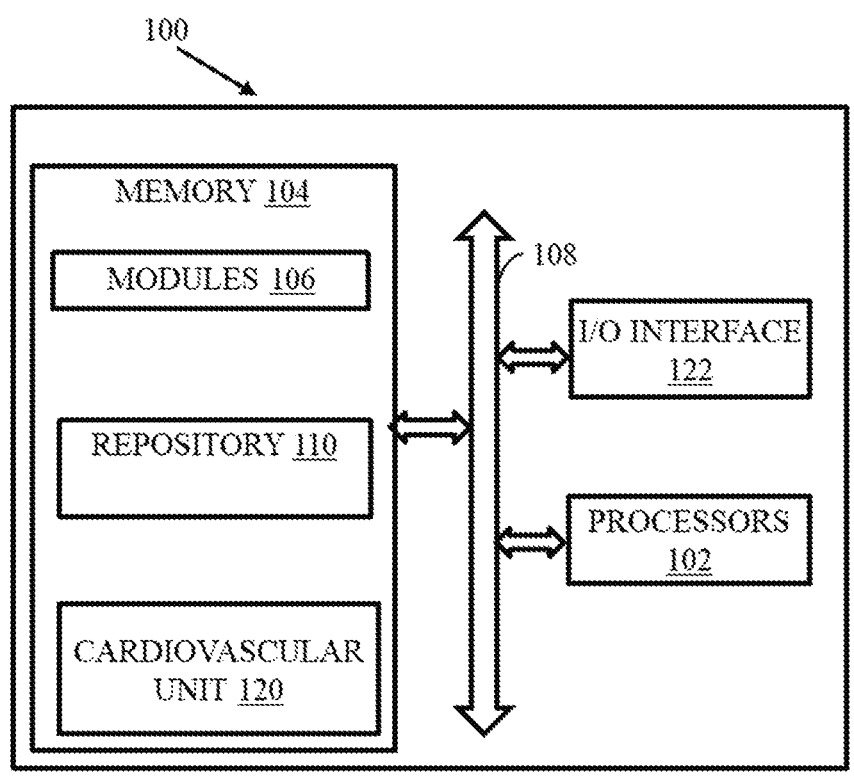
FIG. 1 is a functional block diagram of a system for pressure autoregulation based synthesizing of Photoplethysmogram (PPG) signal, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Embodiments herein provide a method and system for pressure autoregulation based synthesizing of Photoplethysmogram (PPG) signal. The system for pressure autoregulation based synthesizing of PPG signal can generate a plurality of synthetic PPG signals corresponding to a plurality of disease conditions by varying a plurality of parameters. A digital twin of cardiovascular system is modelled to generate the plurality of synthetic PPG signals corresponding to the plurality of disease conditions. The plurality of synthetic PPG signals can be used to tune Machine Learning algorithms. Further, the plurality of synthetic PPG signals can be utilized to understand, analyze and classify cardiovascular disease progression. An implementation of the method and system for pressure autoregulation based synthesizing of PPG signal is described further in detail with reference to FIGS. 1 through 5G.

Referring now to the drawings, and more particularly to FIG. 1 through 5G, where similar reference characters denote corresponding features consistently throughout the figures, there are shown preferred embodiments and these embodiments are described in the context of the following exemplary system and/or method.

FIG. 1 is a functional block diagram of a system for pressure autoregulation based synthesizing of PPG signal, according to some embodiments of the present disclosure. The system 100 includes or is otherwise in communication with one or more hardware processors, such as a processors 102, at least one memory such as a memory 104, an I/O interface 122. The memory 104 may include the cardiovascular model 120. The processor 102, memory 104, and the I/O interface 122 may be coupled by a system bus such as a system bus 108 or a similar mechanism.

The I/O interface 122 may include a variety of software and hardware interfaces, for example, a web interface, a graphical user interface, and the like. The interface 122 may include a variety of software and hardware interfaces, for example, interfaces for peripheral device(s), such as a keyboard, a mouse, an external memory, a plurality of sensor devices, a printer and the like. Further, the interface 122 may enable the system 100 to communicate with other devices, such as web servers and external databases.

The interface 122 can facilitate multiple communications within a wide variety of networks and protocol types, including wired networks, for example, local area network (LAN), cable, etc., and wireless networks, such as Wireless LAN (WLAN), cellular, or satellite. For the purpose, the interface 122 may include one or more ports for connecting a number of computing systems with one another or to another server computer. The I/O interface 122 may include one or more ports for connecting a number of devices to one another or to another server.

The hardware processor 102 may be implemented as one or more microprocessors, microcomputers, microcontrollers, digital signal processors, central processing units, state machines, logic circuitries, and/or any devices that manipulate signals based on operational instructions. Among other capabilities, the hardware processor 102 is configured to fetch and execute computer-readable instructions stored in the memory 104.

The memory 104 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 104 includes a plurality of modules 106 and a repository 110 for storing data processed, received, and generated by one or more of the modules 106 and a cardiovascular unit 120. The cardiovascular unit includes a cardiovascular model (not shown in FIG. 1) and other modules (not shown in FIG. 1). The modules 106 may include routines, programs, objects, components, data structures, and so on, which perform particular tasks or implement particular abstract data types.

The memory 104 also includes module(s) 106 and a data repository 110. The module(s) 106 include programs or coded instructions that supplement applications or functions performed by the system 100 for pressure autoregulation based synthesizing of PPG signal. The modules 106, amongst other things, can include routines, programs, objects, components, and data structures, which perform particular tasks or implement particular abstract data types. The modules 106 may also be used as, signal processor(s), state machine(s), logic circuitries, and/or any other device or component that manipulates signals based on operational instructions. Further, the modules 106 can be used by hardware, by computer-readable instructions executed by a processing unit, or by a combination thereof. The modules 106 can include various sub-modules (not shown). The modules 106 may include computer-readable instructions that supplement applications or functions performed by the system 100 for pressure autoregulation based synthesizing of PPG signal.

The data repository 110 may include a "physionet MIMIC II' data set other data. Further, the other data amongst other things, may serve as a repository for storing data that is processed, received, or generated as a result of the execution of one or more modules in the module(s) 106 and the modules associated with the cardiovascular model 120.

Although the data repository 110 is shown internal to the system 100, it will be noted that, in alternate embodiments, the data repository 110 can also be implemented external to the computing device 100, where the data repository 110 may be stored within a database (not shown in FIG. 1) communicatively coupled to the computing device 100. The data contained within such external database may be periodically updated. For example, new data may be added into the database (not shown in FIG. 1) and/or existing data may be modified and/or non-useful data may be deleted from the database (not shown in FIG. 1). In one example, the data may be stored in an external system, such as a Lightweight Directory Access Protocol (LDAP) directory and a Relational Database Management System (RDBMS). In another embodiment, the data stored in the data repository 110 may be distributed between the computing device 104 and the external database (not shown).

Figure 2:
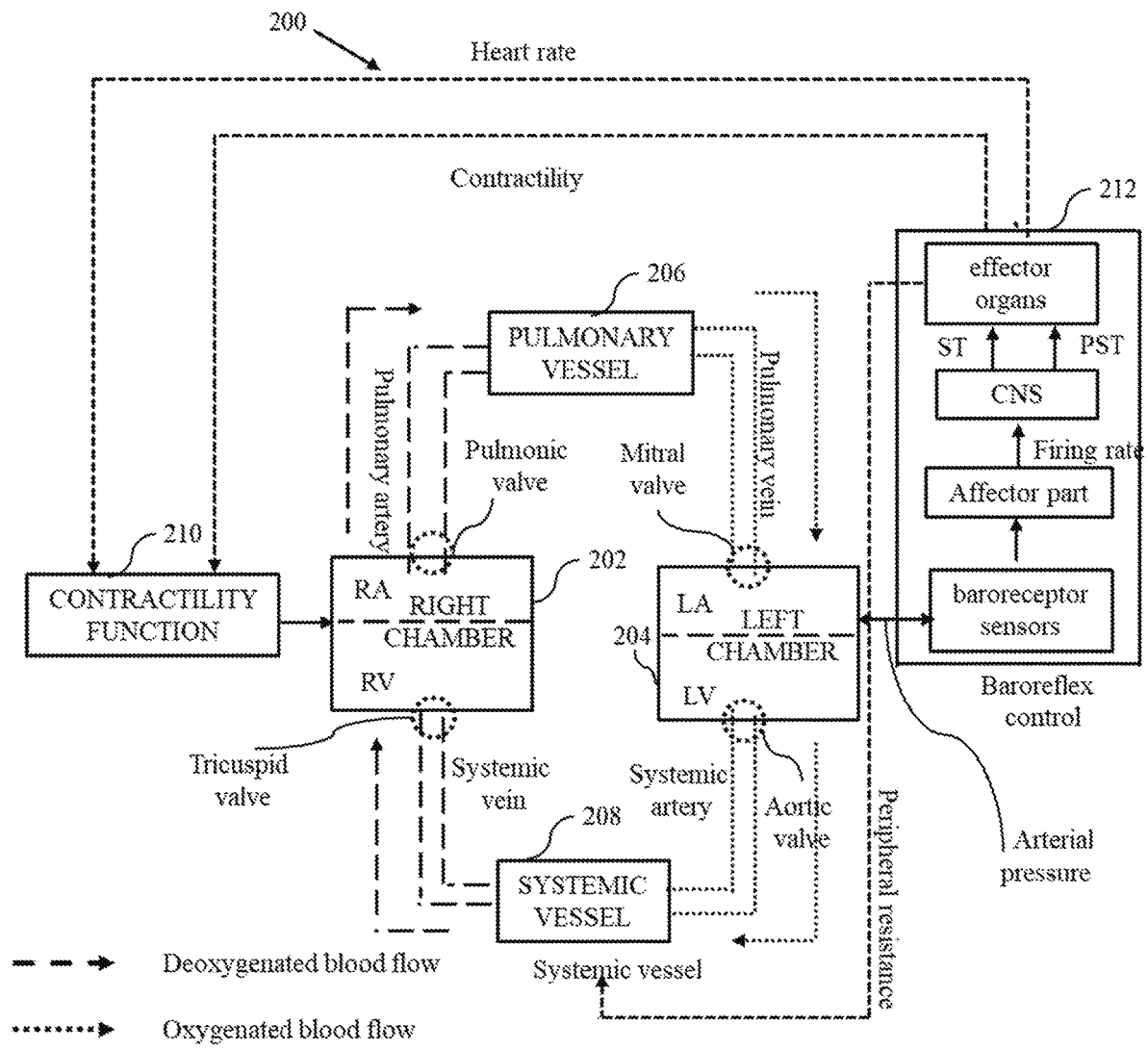
FIG. 2 illustrates an example cardiovascular model for pressure autoregulation based synthesizing of PPG signal, in accordance with some embodiments of the present disclosure.

FIG. 2 illustrates an example cardiovascular model for pressure autoregulation based synthesizing of PPG signal, in accordance with some embodiments of the present disclosure. Now referring to FIG. 2, the cardiovascular model includes a two chambered heart with contractility function 210, a plurality of blood vessels with flow dynamics, and a baroreflex control 212. The two chambered heart includes a right chamber 202 and a left chamber 204. The plurality of blood vessels including a pulmonary vessel 206 and a systemic vessel 208. The right chamber is having a right auricle and a right ventricle. The left chamber includes a left auricle and a left ventricle. The systemic vessel 208 is connected to the right ventricle with a tricuspid valve and systemic vein. The systemic vessel 208 is connected to the left ventricle via aortic valve and systemic artery. The pulmonary vessel 206 is connected to the right auricle via pulmonary valve and pulmonary artery. The pulmonary vessel 206 is connected to the left auricle via mitral valve and pulmonary vein. The pulmonary vessel 206 is connected to the right auricle via pulmonic valve and pulmonary artery. The pulmonary artery and systemic vein carries deoxygenated blood. The systemic artery and pulmonary vein carries oxygenated blood. In an embodiment, the cardiovascular model is simulated using Simulink.

In an embodiment, the baroreflex control mechanism 212 is adapted from pulsatile heart and vascular dynamics. The Baroreflex control mechanism is implemented using three different controllers to capture the effect of aortic pressure variation, namely, a controller to adjust the total systemic arterial resistance or vascular tone, heart rate and a contractility controller. The Baroreflex control mechanism is associated with a feedback mechanism. The feedback mechanism is divided in three parts: (i) affector part, denoting the baroreceptors, for sensing any change in arterial pressure through change in cross sectional area of carotid sinus region and generates a firing rate. (ii) The Central Nervous System (CNS), generates sympathetic and parasympathetic nerve activities depending on the firing rate of affector parts and is fed to effector organs. (iii) The effector organs are the target areas controls heart rate, contractility and peripheral resistance to regulate blood pressure across the plurality of blood vessels.

In an embodiment, the ventricles of the cardiovascular model are modeled as compliant vessels with dynamic compliance property. During diastole, the compliance increases accommodating larger volume of blood. During systole, the compliance decreases, becoming rigid to contract ejecting blood with higher pressure. Flow equations are given in equations 1 to 6.

$$V_{SA}(t) = V_{d,SA} + C_{SA}P_{SA}(t) \tag{1}$$

$$V_{LV}(t) = V_{d,LV} + C_{LV}(t)P_{LV}(t) \tag{2}$$

$$V_{RV}(t) = V_{d,RV} + C_{RV}(t)P_{RV}(t) \tag{3}$$

$$d\frac{V_{SA}}{dt} = Q_{AO} - Q_{SA} \tag{4}$$

$$d\frac{V_{LV}}{dt} = Q_{Mi} - Q_{Ao} \tag{5}$$

$$d\frac{V_{RV}}{dt} = Q_{TC} - Q_{PV} \tag{6}$$

where, V, C, P and Q represents volume, compliance, pressure and flow through various compartments, subscript SA indicates systemic artery, LV represents Left ventricle and RV is right ventricle, Ao is aorta, Mi is mitral valve, Tc is tricuspid valve and PV is pulmonary vein.

In an embodiment, the blood pressure control is an integral component of cardiovascular system which operates in a feedback mechanism, regulating pressure, thereby regulating flow, heart rate and vascular tone. The feedback mechanism for controlling blood pressure is performed by utilizing a baroreflex feedback mechanism. The baroreflex controller of the baroreflex mechanism is sensitive to changes in aortic pressure, sensed through baroreceptors placed mainly at carotid sinus region.

Figure 3:
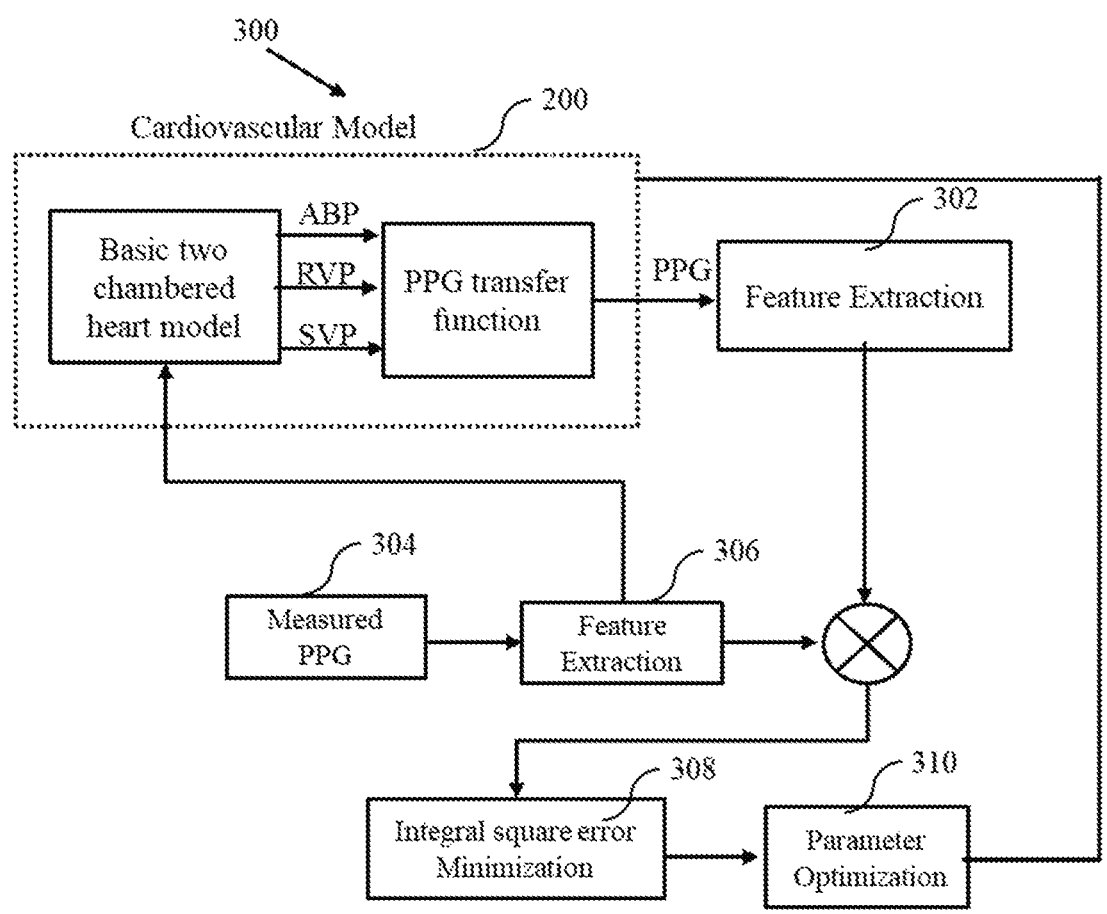
FIG. 3 is an example block diagram illustrating a method for pressure autoregulation based synthesizing of PPG signal, in accordance with some embodiments of the present disclosure.

FIG. 3 is an example block diagram illustrating a method for pressure autoregulation based synthesizing of PPG signal, in accordance with some embodiments of the present disclosure.

Now referring to FIG. 3, initially, a PPG cycle duration is learned from a PPG signal obtained from the database. The PPG transfer function of the cardiovascular model 200 generates the synthetic PPG signal based on Arterial Blood Pressure (ABP), Right Ventricular Pressure (RVP) and Systemic Ventricular Pressure (SVP). Further, the measured PPG signal 304 is directly fed back to the cardiovascular model 200 to control the total duration of the heart cycle. Based on this feedback, the estimated PPG from the cardiovascular model 200 is regenerated. Further, remaining set of features 306 are evaluated from both estimated or synthesized PPG and measured PPG, Feature set of the estimated PPG (fest) 302 and the measured PPG (fmea) 306 are denoted as $[f_1^e, f_2^e, f_3^e, f_4^e]$ and $[f_1^m, f_2^m, f_3^m, f_4^m]$ respectively. In order to tune the various parameters $K_1$, $K_2$, $td_1$ and $td_2$ associated with the synthetic PPG signal, the integral-squared-error (ISE) of each element of the feature set is minimized using particle-swarm-optimization (PSO) algorithm which can be analytically be defined as given in equation 7:

$$e_i = \int_0^t [f_i^m - f_i^e]^2; f_i \in [1,2,3,4] \quad (7)$$

The cardiovascular unit 120 of the system 100 is configured to, receive a plurality of systolic phase parameters and a plurality of diastolic phase parameters associated with the cardiovascular model. The systolic phase parameters comprising a systolic time delay, a systolic lag constant, a systolic gain and a systemic arterial pressure. The diastolic phase parameters comprising a diastolic time delay, a diastolic lag constant, a diastolic gain and a pressure difference between the right ventricle and the systemic vein.

Further, the cardiovascular unit 120 of the system 100 is configured to compute, a systolic phase of a PPG signal based on the plurality of systolic phase parameters by utilizing a systolic contractility function and a baroreflex control. The systolic contractility function includes a plurality of systolic time constants, a systolic duration and a cardiac cycle duration. The systolic phase parameters comprising a systolic time delay, a systolic lag constant, a systolic gain and a systemic arterial pressure. The systemic arterial pressure is computed based on a compliance of the systemic artery and a volume associated with the systemic artery.

In an embodiment, Contractility function 210 of FIG. 2 is the driving block of the model, generating time varying functions which causes change in contraction pattern, bringing the pump like action of heart. The contractility function 210 is modeled as two periodic piecewise functions, depicting low compliance ventricular systole (VS) and high compliance ventricular diastole (VD). The systolic contractility function is given in equation 8.

$$C_V(t) = C_{VD} * \left(\frac{C_{VS}}{C_{VD}}\right)^{\frac{1-e^{-t/\tau_S}}{1-e^{T_S/\tau_S}}}; \quad (8)$$

$$0 \leq t_S \leq T_S$$

Here, the transitions are determined by the time constants $\tau_S$ and $\tau_D$, $T_S$ is the systole duration and T is the cardiac cycle duration.

Further, the cardiovascular unit 120 of the system 100 is configured to compute, a diastolic phase of the PPG signal based on a plurality of diastolic phase parameters by utilizing a diastole contractility function. The diastolic contractility function includes a plurality of diastolic time constants, a diastolic duration and the cardiac cycle duration. The diastolic phase parameters comprising a diastolic time delay, a diastolic lag constant, a diastolic gain and a pressure difference between the right ventricle and the systemic vein. The right ventricular pressure is computed based on a compliance of the right ventricle and a volume associated with the right ventricle. The pressure on the systemic vein is computed based on a compliance of the systemic vessel and a volume associated with the systemic vessel. The diastolic contractility function is given in equation 9.

$$C_V(t) = C_{VS} * \left(\frac{c_{Vs}}{c_{VD}}\right)^{\frac{1-e^{-(t-\tau_S)/\tau_D}}{1-e^{-\frac{T-T_S}{\tau_D}}}}; \quad (9)$$

$$T_S \leq t \leq T$$

Here, the transitions are determined by the time constants $\tau_S$ and $\tau_D$, $T_S$ is the systole duration and T is the cardiac cycle duration.

Further, the cardiovascular unit 120 of the system 100 is configured to generate by the one or more hardware processors, a synthetic PPG signal based on the computed systolic phase and the diastolic phase of the PPG signal, wherein the synthetic PPG signal is associated with the plurality of the synthetic PPG signal parameters. The plurality of synthetic PPG signal parameters includes a cycle duration, a systolic peak amplitude, a systolic peak location, a diastolic notch amplitude and a diastolic notch location.

In an embodiment, the method of computing the systolic phase of the PPG signal, computing the diastolic phase of the PPG signal and generating the synthetic PPG signal by utilizing the computed systolic phase and the diastolic phase are performed by utilizing the cardiovascular model as explained in FIG. 2.

In an embodiment, the cardiovascular model generates regulated arterial pressure (Pa) and flow in different compartments. The synthetic PPG signal is modeled from systemic flow or even from arterial pressure signal as PPG has a strong correlation with the blood flow in systemic arteries. The cardiovascular model has been developed as an analytical model to simulate the PPG signal from the arterial pressure and the model is given in equation 10.

$$PPG = K_1 \frac{e^{-S \cdot td_1}}{1 + T_1 S} P_{SA} + K_2 e^{-S \cdot td_2}(P_{RV} - P_{SV}) \quad (10)$$

where $td_1$, $td_2$ are systolic and diastolic time delays, $K_1$ and $K_2$ are systolic and diastolic gains $T_1$ is the lag constant. $P_{SA}$, $P_{RV}$ and $P_{SV}$ are the pressure on the systemic artery, right ventricle and systemic vein respectively. The synthetic PPG signal represents two separate flow; the left ventricular contraction causing intra-arterial pulse pressure wave in proximal aorta, which can be modeled from Arterial Blood Pressure (ABP) waveform and the reverse flow during ventricular filling which give rise to dicrotic notch and the flow thereby, modeled by introducing closure of aortic and pulmonary valve. Arbitrary selection of $K_1$, $K_2$, $td_2$ and $td_2$ can give a PPG-like signal.

Further, the cardiovascular unit 120 of the system 100 is configured to simultaneously fetch, by the one or more hardware processors, a plurality of predetermined morphological features associated with a PPG signal from a database. The database includes the "physionet MIMIC II" database.

In an embodiment, in order to generate near natural PPG signals, an estimation algorithm has been implemented, which calculates specific morphological features from a standard PPG signal, extracted from "physionet MIMIC II" data base and optimize the parameters of the synthetic PPG. The feature set consists of PPG cycle duration, PPG systolic peak amplitude (f1) and location (f2), PPG diastolic notch amplitude (f3) and location (f4).

Further, the cardiovascular unit 120 of the system 100 is configured to optimize, by the one or more hardware processors, the plurality of synthetic PPG signal parameters to obtain a plurality of optimized parameters by utilizing the plurality of predetermined morphological features.

Further, the cardiovascular unit 120 of the system 100 is configured to generate, by the one or more hardware processors, the plurality of synthetic PPG signals corresponding to the plurality of disease conditions by varying the plurality of parameters, wherein the plurality of parameters includes the plurality of optimized parameters and a plurality of cardiovascular model parameters. The cardiovascular model parameters includes a valve resistance, a capillary resistance, the time constants, the pressure in the blood vessels, a cardiovascular compliance and vessel compliance.

In an embodiment, the synthetic PPG signal is derived from pressure and flow equations, utilizing a transfer function which links flow variation a source location and a sink or measurement location. For example, the source location can be an aorta and the sink location can be a finger artery.

In an embodiment, the blood flow in the plurality of blood vessels is modeled as laminar flow through a tube like structure, generated due to pressure gradient at source (P1) and sink (P2). The cardiovascular model includes resistive and compliant vessels. Large systemic arteries are usually elastic or compliant and have the capacity to store pressure, while smaller vessels in microcirculation are modeled as resistive vessels. Flow equations through the vessels are as given in equation 11 to 13.

$$Q = \frac{P_1 - P_2}{R} \quad (11)$$

$$R = \frac{8\eta L}{\pi r^4}. \quad (12)$$

$$C\frac{dp}{dt} = Q_1 - Q_2 \quad (13)$$

where, Q is the flow (Q1 and Q2 being flow at any two location), R is the vascular resistance, 'L' is the vessel length, 'h' is blood viscosity, 'r' is the vessel radius, 'P' is the pressure and 'C' is the compliance of vessel.

Figure 4A:
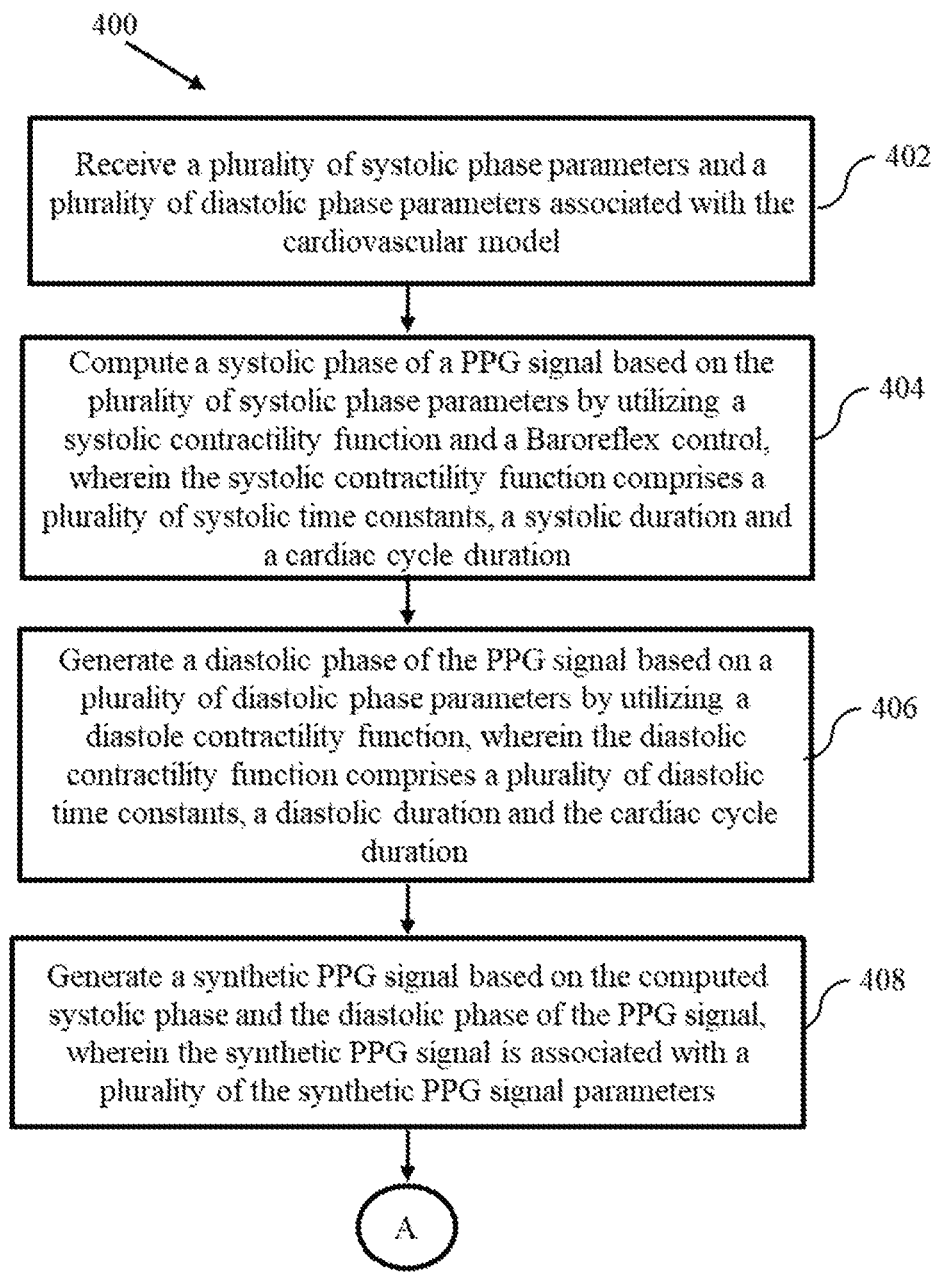
FIGS. 4A and 4B are exemplary flow diagrams for a processor implemented method for pressure autoregulation based synthesizing of PPG signal, according to some embodiments of the present disclosure.
Figure 4B:
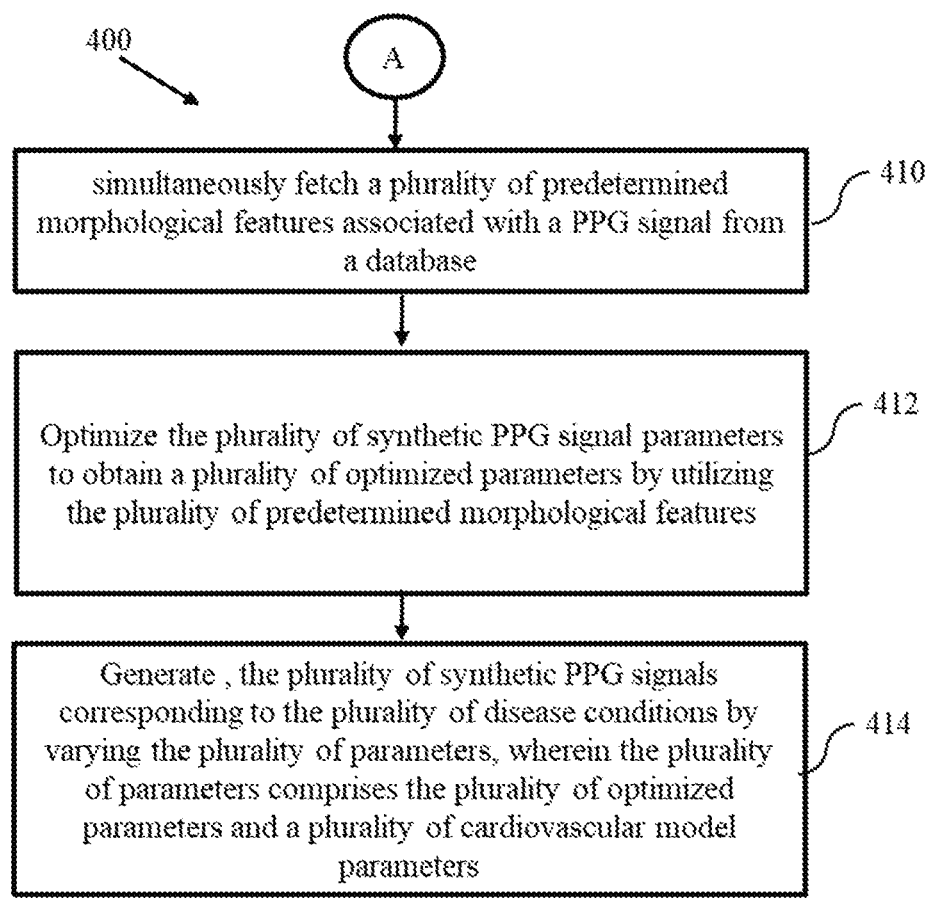

FIGS. 4A and 4B are exemplary flow diagrams for a processor implemented method for pressure autoregulation based synthesizing of PPG signal, according to some embodiments of the present disclosure. The method 400 may be described in the general context of computer executable instructions. Generally, computer executable instructions can include routines, programs, objects, components, data structures, procedures, modules, functions, etc., that perform particular functions or implement particular abstract data types. The method 400 may also be practiced in a distributed computing environment where functions are performed by remote processing devices that are linked through a communication network. The order in which the method 400 is described is not intended to be construed as a limitation, and any number of the described method blocks can be combined in any order to implement the method 400, or an alternative method. Furthermore, the method 400 can be implemented in any suitable hardware, software, firmware, or combination thereof.

At 402, the method 400, receives, by a one or more hardware processors, a plurality of systolic phase parameters and a plurality of diastolic phase parameters associated with the cardiovascular model (shown in FIG. 2). The systolic phase parameters comprising a systolic time delay, a systolic lag constant, a systolic gain and a systemic arterial pressure. The diastolic phase parameters comprising a diastolic time delay, a diastolic lag constant, a diastolic gain and a pressure difference between the right ventricle and the systemic vein. At 404, the method 400, computes, by a one or more hardware processors, a systolic phase of a PPG signal based on the plurality of systolic phase parameters by utilizing a systolic contractility function and a baroreflex control. The systolic contractility function includes a plurality of systolic time constants, a systolic duration and a cardiac cycle duration. The systolic phase parameters comprising a systolic time delay, a systolic lag constant, a systolic gain and a systemic arterial pressure. The systemic arterial pressure is computed based on a compliance of the systemic artery and a volume associated with the systemic artery. At 406, the method 400, computes, by a one or more hardware processors, a diastolic phase of the PPG signal based on a plurality of diastolic phase parameters by utilizing a diastole contractility function, The diastolic contractility function includes a plurality of diastolic time constants, a diastolic duration and the cardiac cycle duration. The diastolic phase parameters comprising a diastolic time delay, a diastolic lag constant, a diastolic gain and a pressure difference between the right ventricle and the systemic vein. The right ventricular pressure is computed based on a compliance of the right ventricle and a volume associated with the right ventricle. The pressure on the systemic vein is computed based on a compliance of the systemic vessel and a volume associated with the systemic vessel. At 408, the method 400, generates, by a one or more hardware processors, by the one or more hardware processors, the synthetic PPG signal based on the computed systolic phase and the diastolic phase of the PPG signal, wherein the synthetic PPG signal is associated with the plurality of the synthetic PPG signal parameters. The plurality of synthetic PPG signal parameters includes a cycle duration, a systolic peak amplitude, a systolic peak location, a diastolic notch amplitude and a diastolic notch location. At 410, the method 400, simultaneously fetch, by a one or more hardware processors, by the one or more hardware processors, a plurality of predetermined morphological features associated with a PPG signal from a database. The database includes the "physionet MIMIC II" database. At 412, the method 400, optimizes, by a one or more hardware processors, by the one or more hardware processors, the plurality of synthetic PPG signal parameters to obtain a plurality of optimized parameters by utilizing the plurality of predetermined morphological features. At 414, the method 400, generates, by a one or more hardware processors, by the one or more hardware processors, the plurality of synthetic PPG signals corresponding to the plurality of disease conditions by varying the plurality of parameters, wherein the plurality of parameters includes the plurality of optimized parameters and a plurality of cardiovascular model parameters. The cardiovascular model parameters includes a valve resistance, a capillary resistance, the time constants, the pressure in the blood vessels, a cardiovascular compliance and vessel compliance.

FIG. 5A to 5G illustrates experimental results for the method for pressure autoregulation based synthesizing of PPG signal, in accordance with some embodiments of the present disclosure.

Figure 5A:
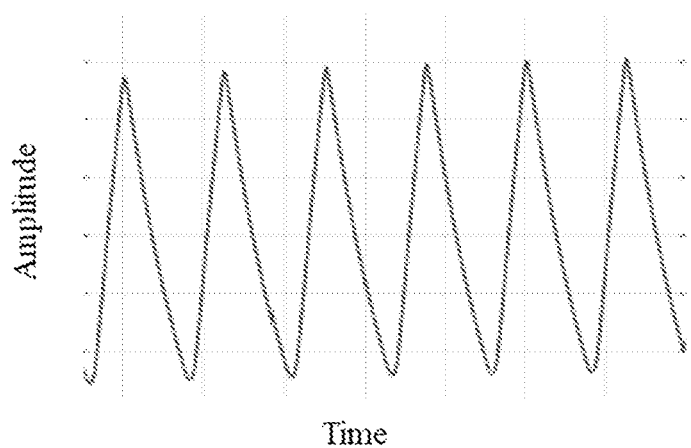
FIG. 5A to 5G illustrates experimental results for the method for pressure autoregulation based synthesizing of PPG signal, in accordance with some embodiments of the present disclosure.
Figure 5B:
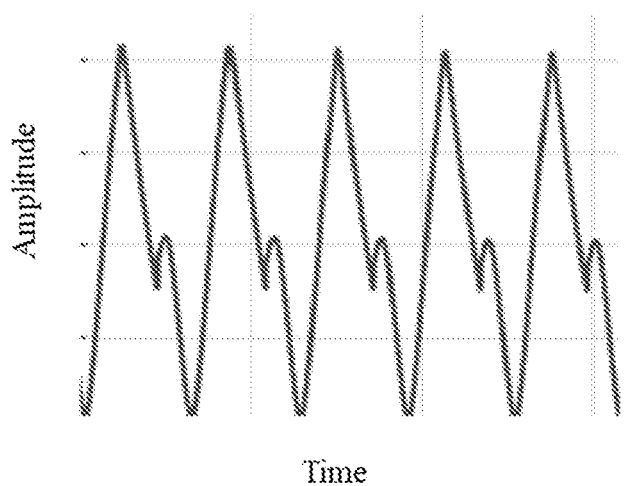

FIG. 5A depicts the synthetic PPG signal estimate from ABP. FIG. 5B depicts the synthetic PPG signal with diastolic event, estimated from ABP and reflected pressure wave, where signal incorporates dicrotic notch and definite systole, diastole events.

Figure 5C:
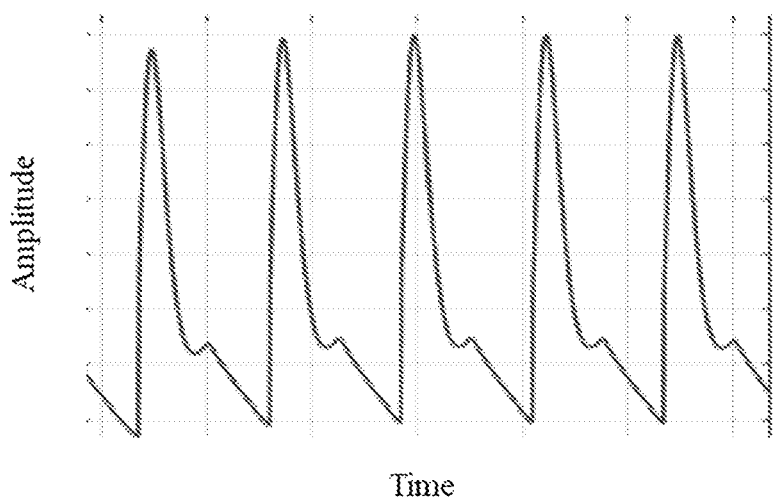

FIG. 5C depicts the synthetic PPG signal after parameter optimization. A plurality of PPG templates can be generated using the same model by varying the feature parameters within the statistical distribution, which is learned during the process of parameter optimization. Further, the plurality of cardiovascular parameters like systemic resistance, aortic resistance, blood viscosity, etc, can be varied to generate the plurality of PPG templates corresponding to a plurality of disease cases. In an embodiment, the plurality of generated PPG templates can be can be further exploded in statistical domain to generate large scale synthetic data.

In an embodiment, a plurality of time series features are extracted from the standard PPG signals and the distribution of the standard PPG signals are analyzed in order to validate the signal characteristics of synthesized PPG, both for healthy and diseased template. The data set for Coronary Artery disease (CAD) and non-CAD subjects are taken from the "physionet MIMIC II" database and compared with the signal characteristics with that of the synthesized PPG template. Explored features includes important statistical information regarding inherent properties of the synthetic PPG signal, which help in discriminating a healthy subject from a diseased one. To obtain a precise and comprehensive calibration, some measures are calculated on both the raw time series data, as well as the remaining time series after de-trending and de-seasonalizing. A total of thirteen measures are extracted from all the time series including seven on the 'raw' data and six on the TSA (trained and seasonally adjusted) data. List of measures are provided in Table I.

TABLE I

| Feature | Raw | TSA |
|---|---|---|
| Trend | | Yes |
| Sasonality | | Yes |
| Serial Correlation | | Yes |
| Non-linearity | Yes | Yes |
| Skewness | Yes | Yes |
| Kurtosis | Yes | Yes |
| Self Similarity | Yes | |
| Periodicity | Yes | |

TABLE I-continued

| Feature | Raw | TSA |
|---|---|---|
| Average Maharaj distance | Yes | |
| Number of direction changes | Yes | |

Suppose the i-th feature in CAD and non CAD is denoted as $F_i^C$ and $F_i^{NC}$ respectively, where i=1,2 . . . 13, a non-parametric density function can be fit to both of CAD and non-CAD by utilizing kernel density estimation. Further, a Gaussian kernel can be utilized to fit a non-parametric distribution. Thus, two distributions are fitted, say $f_i^C$ and $f_i^{NC}$ to $F_i^C$ and $F_i^C$ respectively. To discriminate CAD and non CAD features, similarity between $f_i^C$ and $f_i^{NC}$ needs to be calculated as if these class shows similar features, two classes can not be discriminated. This necessitates a measure of dissimilarity between two distributions, and a Matusita distance is utilized in measuring the likeness, or lack of it, between $f_i^C$ and $f_i^{NC}$.

In an embodiment, the Matusita distance is a measure of divergence between two statistical distributions. A Bhattacharya distance is a more popular measure of dissimilarity between two distributions. However, its range is [0, ∞]. The Matusita distance is a transformation of Bhattacharya distance such that the range is transformed to [0,2]. For two kernel density estimates, say P and Q respectively, there are 'd' observable points for each density. The Matusita distance is given in equation 14.

$$d_M = \Sigma_{j=1}^d (\sqrt{P_j} - \sqrt{Q_j})^2 = 2 - 2\Sigma_{j=1}^d \sqrt{P_j Q_j} \quad (14)$$

In an embodiment, a practical advantage of Matusita distance is that this measure tends to suppress high separability values, whilst overemphasizing low separability values.

In an embodiment, the features for which the Matusita distance between CAD and non CAD density is less than 1 are eliminated to reduce the number of features to 10 (Average Maharaj distance, which is only for raw data, and skewness, which is for both raw and TSA, are discarded). Hence, ten decisions are obtained, each for one feature. The final class, CAD or non CAD, is decided based on the majority rule. Now for the synthesized PPG template, ten statistical features are extracted in the same way. For each feature, the probabilities of the feature belonging to the corresponding CAD and non-CAD distributions are calculated. Further, a new value is assigned to the distribution corresponding to larger probability.

In an embodiment, the cardiovascular model is experimented as follows: Two specific templates, naming healthy and atherosclerosis PPG have been generated by the cardiovascular model and the template PPG signals have also been used to cluster CAD, non CAD data from "physionet MIMIC II" dataset as an initial validation of the process.

Figure 5D:
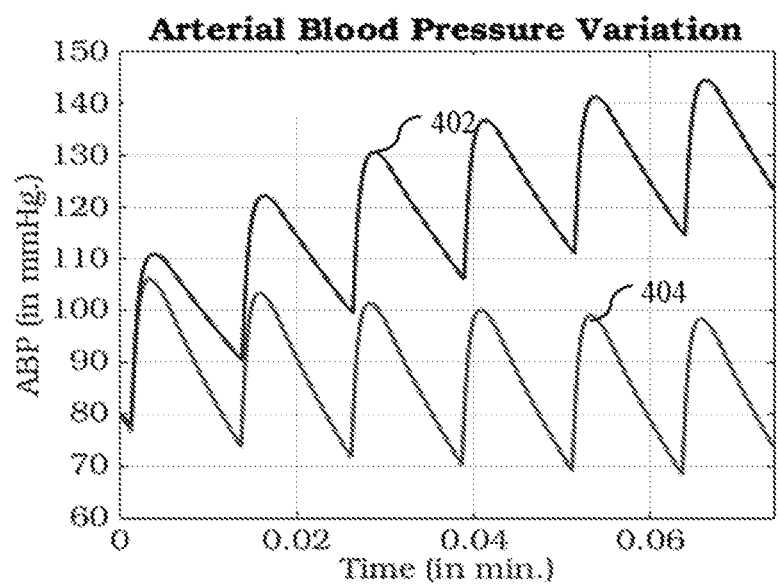
Figure 5E:
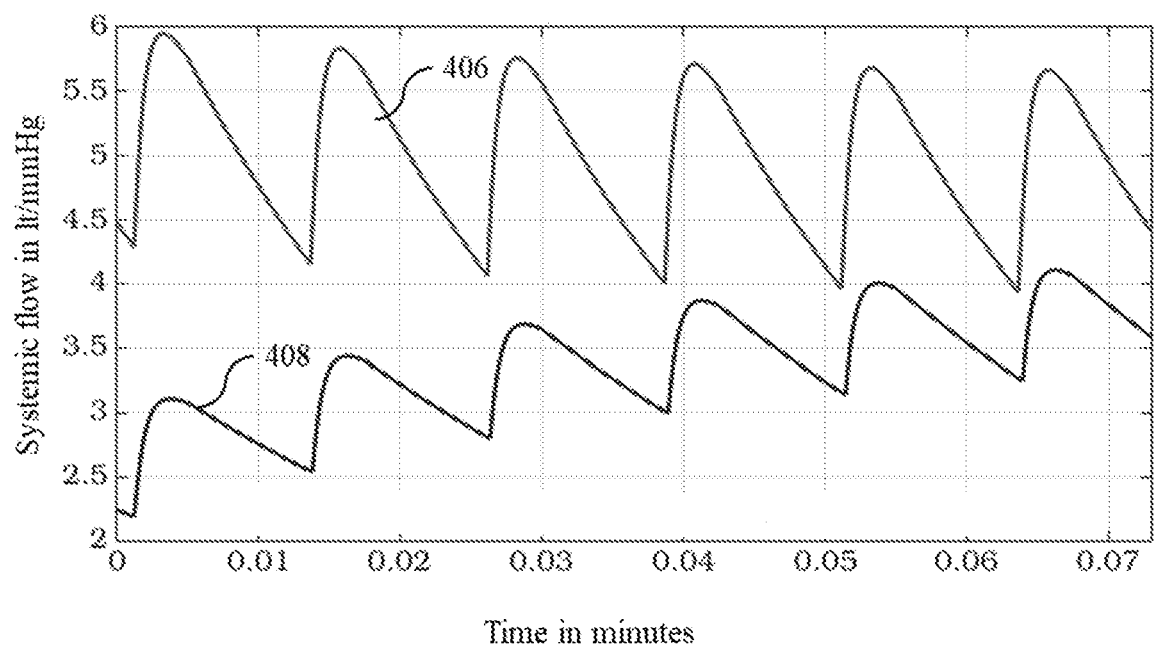
Figure 5F:
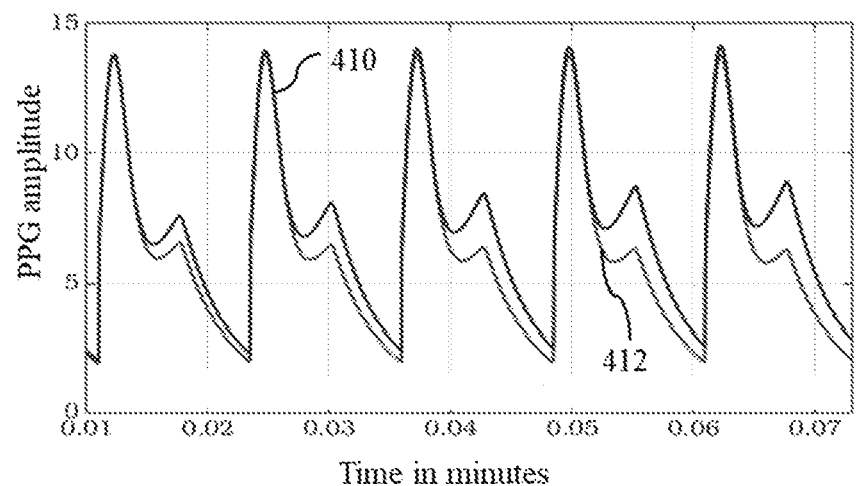

In an embodiment, the cardiovascular model can generate different PPG templates as per requirement, mainly by changing and tuning the plurality of physiological parameters of the model. For an initial validation, two specific PPG templates have been generated, one corresponding to healthy subject, that is modeling the plurality of cardiovascular parameters like blood pressure, flow, viscosity, etc. as per healthy range and another diseased template. Disease template represents Atherosclerosis condition. Atherosclerosis is a vascular disease resulting in narrowing of blood vessels due to plaque deposition in vascular wall. Pathophysiologically, systemic resistance to blood flow increases for Atherosclerosis patients. In the cardiovascular model, healthy and atherosclerosis templates are generated by changing the equivalent systemic resistance from 'R' in healthy subject to '2R' for atherosclerosis subject. Guided by the medical literature, a very simplified representation of Atherosclerosis condition has been performed, to verify the difference in output generated by the model. FIGS. 5D, 5E and 5F depicts the change in arterial pressure, systemic flow and generated PPG for healthy and Atherosclerosis class.

FIG. 5D illustrates a graph indicating variation in arterial pressure for healthy subject and atherosclerosis subject. Here, the time is taken along x-axis and ABP is taken along y-axis The plot 504 indicates the arterial pressure for normal subject with normal systemic resistance (R) and the plot 502 indicates the arterial pressure for the atherosclerosis subject with abnormal systemic resistance (2R). Now referring to FIG. 5D, arterial blood pressure for healthy subjects in the simulation result varies in the range of 80 to 110 mm of Hg, regulated by the baroreflex control mechanism. On introducing the diseased condition (2R), blood pressure shoots up to 110 to 140 mm of Hg, a characteristic often noticed in subjects with Atherosclerosis. Another interesting feature is the breakdown of auto-regulation mechanism. For healthy template, pressure waveform settles to a controlled value after few initial cardiac cycle, but the diseased template fails to reach equilibrium condition. This indicates that for elevated disease condition, baroreflex mechanism alone cannot regulate blood pressure and other regulatory mechanisms like vaso-control or renal control needs to be incorporated to regulate the elevated conditions.

FIG. 5E illustrates a graph indicating variation in systemic flow for healthy subject and atherosclerosis subject. Here, the time is taken along x-axis and systemic flow is taken along y-axis. The plot 506 indicates the systemic flow for normal subject with normal systemic resistance (R) and the plot 508 indicates the systemic flow for the atherosclerosis subject with abnormal systemic resistance (2R).

Now referring to FIG. 5E, the systemic flow is much reduced in diseased template for obvious reason. In Atherosclerosis, lumen diameter decrease and flow gets restricted, and these phenomenon has been correctly replicated by the model.

FIG. 5F illustrates a graph indicating variation in generated PPG signal for healthy subject and atherosclerosis subject. Here, the time is taken along x-axis and amplitude of the synthetic PPG signal is taken along y-axis. The plot 512 indicates the synthetic PPG signal for normal subject with normal systemic resistance (R) and the plot 510 indicates the synthetic PPG signal for the atherosclerosis subject with abnormal systemic resistance (2R). The PPG templates generated by the model for healthy and diseased shows very interesting characteristics. PPG signal nature in systolic cycle is similar in both cases, but during diastole, peak diastolic amplitude increases in Atherosclerosis simulation. Pathophysiological reason behind this observation is that cardiac mechanism tries to keep cardiac output constant. Cardiac output is the product of heart rate and stroke volume. As the arteries gets constricted due to increased systemic resistance, heart tries to pump more blood, increasing stroke volume, hence an increased diastolic peak is observed in the synthetic PPG.

In an embodiment, the CAD estimation is performed as follows: CAD is a case of Atherosclerosis condition where arteries supplying blood to heart muscle gets hardened and narrowed. PPG being a peripheral measurement technique, conditions due to change in coronary artery may not be morphologically evident, but statistical distribution of the signal may vary. Under this hypothesis, we check statistical features for CAD and non CAD data measured from the subject under test and compare the feature distribution for the template generated from our model. Atherosclerosis (2R) template is regarded as CAD case and healthy template (R) is regarded as non CAD case.

In an embodiment, the CAD is a case of Atherosclerosis condition where arteries supplying blood to heart muscle gets hardened and narrowed. PPG being a peripheral measurement technique, conditions due to change in coronary artery may not be morphologically evident, but statistical distribution of the signal may vary. Under this hypothesis, the statistical features for CAD and non CAD data measured from patients are checked and compared with the feature distribution for the template generated from the cardiovascular model. Atherosclerosis (2R) template is regarded as CAD case and healthy template (R) is regarded as non CAD case.

For a generated CAD PPG (diseased condition), the present disclosure shows that nine out of ten features are classified as CAD, thus leading to the conclusion that the generated CAD PPG tallies well with a real CAD PPG. However, for a generated non CAD PPG (assumed to be healthy), the picture is ambiguous. Four features are assigned to non-CAD distribution, while six are identified as CAD. These four features are trend, seasonality, non-linearity (for TSA data) and self-similarity. For a sample plot, the positions of generated feature value of trend with respect to its corresponding CAD and non-CAD distributions are shown in FIG. 5G.

Figure 5G:
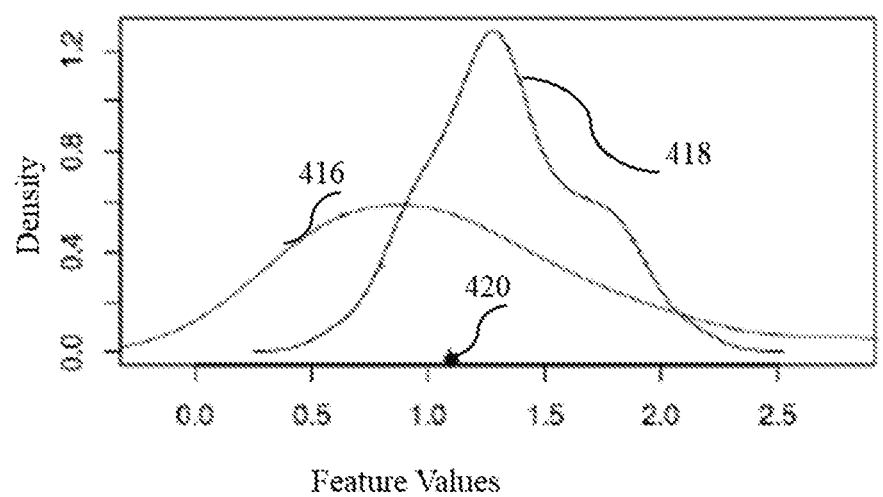

FIG. 5G illustrates a graph indicating position of differentiating trend feature value for CAD and non-CAD subjects. Here, the graph is plotted by taking feature values in x-axis and density of features in y-axis. The point 520 indicates the position of the differentiating trend feature value. The plot 518 indicates the feature values for non-CAD subjects and the plot 516 indicates the feature values for CAD subject.

In an embodiment, the Reason for high accuracy of classifying CAD as CAD and low accuracy of healthy template as non CAD in feature domain may be due to the fact that there is essentially no 'healthy' subject in the database. Non-CAD do not refer to healthy subject or the healthy template that has been generated by the model, rather it signifies that the subject may have other cardiovascular disease apart from CAD.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein addresses unresolved problem of generating the plurality of synthetic PPG signals corresponding to a plurality of disease conditions. Here a digital twin of the cardiovascular model has been implemented with pressure autoregulation using Simulink. Further, the system 100 can be utilized to train the Machine Learning model is analyzing and diagnosing based on the PPG signals pertaining to various disease conditions.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e. non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method, the method comprising:
    receiving, by a one or more hardware processors, a plurality of systolic phase parameters and a plurality of diastolic phase parameters associated with a cardiovascular model;
    computing, by the one or more hardware processors, a systolic phase of a PPG signal based on the plurality of systolic phase parameters by utilizing a systolic contractility function and a baroreflex control, wherein the systolic contractility function comprises a plurality of systolic time constants, a systolic duration and a cardiac cycle duration;
    computing, by the one or more hardware processors, a diastolic phase of the PPG signal based on a plurality of diastolic phase parameters by utilizing a diastole contractility function and the baroreflex control, wherein the diastolic contractility function comprises a plurality of diastolic time constants, a diastolic duration and the cardiac cycle duration;
    generating, by the one or more hardware processors, a synthetic PPG signal based on the computed systolic phase and the diastolic phase of the PPG signal, wherein the synthetic PPG signal is associated with a plurality of the synthetic PPG signal parameters;
    simultaneously fetching, by the one or more hardware processors, a plurality of predetermined morphological features associated with a PPG signal from a database;
    optimizing, by the one or more hardware processors, the plurality of synthetic PPG signal parameters to obtain a plurality of optimized parameters by utilizing the plurality of predetermined morphological features; and
    generating, by the one or more hardware processors, the plurality of synthetic PPG signals corresponding to the plurality of disease conditions by varying the plurality of parameters, wherein the plurality of parameters comprises the plurality of optimized parameters and a plurality of cardiovascular model parameters.

2. The processor implemented method of claim 1, wherein the plurality of predetermined morphological features of the PPG signal comprises a cycle duration, a systolic peak amplitude, a systolic peak location, a diastolic notch amplitude and a diastolic notch location.

3. The processor implemented method of claim 1, wherein the plurality of synthetic PPG signal parameters comprises a cycle duration, a systolic peak amplitude, a systolic peak location, a diastolic notch amplitude and a diastolic notch location.

4. The processor implemented method of claim 1, wherein computing the systolic phase of the PPG signal, computing the diastolic phase of the PPG signal and generating the synthetic PPG signal by utilizing the computed systolic phase and the diastolic phase are performed by utilizing the cardiovascular model.

5. The processor implemented method of claim 1, wherein the cardiovascular model comprising a two chambered heart with contractility function, a plurality of blood vessels with flow dynamics and a baroreflex control, wherein the two chambered heart comprising a right ventricle with a tricuspid valve and pulmonary valve, and a left ventricle with a mitral valve and an aortic valve, wherein a pulmonary vessel is connected to the right ventricle via a pulmonary artery and the pulmonary valve, wherein the pulmonary vessel is connected to the left ventricle via a pulmonary vein and the mitral valve, wherein a systemic vessel is connected to the right ventricle via a systemic vein and the tricuspid valve, wherein the systemic vessel is connected to the left ventricle via a systemic artery and the aortic valve.

6. The processor implemented method of claim 1, wherein the pressure on arteries and veins are regulated by the baroreflex control.

7. The processor implemented method of claim 1, wherein the systolic phase parameters comprising a systolic time delay, a systolic lag constant, a systolic gain and a systemic arterial pressure, wherein the systemic arterial pressure is computed based on a compliance of the systemic artery and a volume associated with the systemic artery.

8. The processor implemented method of claim 1, wherein the diastolic phase parameters comprising a diastolic time delay, a diastolic lag constant, a diastolic gain and a pressure difference between the right ventricle and the systemic vein, wherein the right ventricular pressure is computed based on a compliance of the right ventricle and a volume associated with the right ventricle, wherein the pressure on the systemic vein is computed based on a compliance of the systemic vessel and a volume associated with the systemic vessel.

9. The processor implemented method of claim 1, wherein the cardiovascular model parameters comprises a valve resistance, a capillary resistance, the time constants, the pressure in the blood vessels, a cardiovascular compliance and vessel compliance.

10. A system comprising:
  at least one memory storing programmed instructions;
  one or more hardware processors operatively coupled to the at least one memory, wherein the one or more hardware processors are configured by the programmed instructions to:
    receive a plurality of systolic phase parameters and a plurality of diastolic phase parameters associated with a cardiovascular model;
    compute a systolic phase of a PPG signal based on the plurality of systolic phase parameters by utilizing a systolic contractility function and a baroreflex control, wherein the systolic contractility function comprises a plurality of systolic time constants, a systolic duration and a cardiac cycle duration;
    compute a diastolic phase of the PPG signal based on a plurality of diastolic phase parameters by utilizing a diastole contractility function and the baroreflex control, wherein the diastolic contractility function comprises a plurality of diastolic time constants, a diastolic duration and the cardiac cycle duration;
    generate a synthetic PPG signal based on the computed systolic phase and the diastolic phase of the PPG signal, wherein the synthetic PPG signal is associated with a plurality of the synthetic PPG signal parameters;
    simultaneously fetch a plurality of predetermined morphological features associated with a PPG signal from a database;
    optimize the plurality of synthetic PPG signal parameters to obtain a plurality of optimized parameters by utilizing the plurality of predetermined morphological features; and
    generate the plurality of synthetic PPG signals corresponding to the plurality of disease conditions by varying the plurality of parameters, wherein the plurality of parameters comprises the plurality of optimized parameters and a plurality of cardiovascular model parameters.

11. The system of claim 10, wherein the plurality of predetermined morphological features of the PPG signal comprises a cycle duration, a systolic peak amplitude, a systolic peak location, a diastolic notch amplitude and a diastolic notch location.

12. The system of claim 10, wherein the plurality of synthetic PPG signal parameters comprises a cycle duration, a systolic peak amplitude, a systolic peak location, a diastolic notch amplitude and a diastolic notch location.

13. The system of claim 10, wherein computing the systolic phase of the PPG signal, computing the diastolic phase of the PPG signal and generating the synthetic PPG signal by utilizing the computed systolic phase and the diastolic phase are performed by utilizing the cardiovascular model.

14. The system of claim 10, wherein the cardiovascular model comprising a two chambered heart with contractility function, a plurality of blood vessels with flow dynamics and a baroreflex control, wherein the two chambered heart comprising a right ventricle with a tricuspid valve and pulmonary valve, and a left ventricle with a mitral valve and an aortic valve, wherein a pulmonary vessel is connected to the right ventricle via a pulmonary artery and the pulmonary valve, wherein the pulmonary vessel is connected to the left ventricle via a pulmonary vein and the mitral valve, wherein a systemic vessel is connected to the right ventricle via a systemic vein and the tricuspid valve, wherein the systemic vessel is connected to the left ventricle via a systemic artery and the aortic valve.

15. The system of claim 10, wherein the pressure on arteries and veins are regulated by the baroreflex control.

16. The system of claim 10, wherein the systolic phase parameters comprising a systolic time delay, a systolic lag constant, a systolic gain and a systemic arterial pressure, wherein the systemic arterial pressure is computed based on a compliance of the systemic artery and a volume associated with the systemic artery.

17. The system of claim 10, wherein the diastolic phase parameters comprising a diastolic time delay, a diastolic lag constant, a diastolic gain and a pressure difference between the right ventricle and the systemic vein, wherein the right ventricular pressure is computed based on a compliance of the right ventricle and a volume associated with the right ventricle, wherein the pressure on the systemic vein is computed based on a compliance of the systemic vessel and a volume associated with the systemic vessel.

18. The system of claim 10, wherein the cardiovascular model parameters comprises a valve resistance, a capillary resistance, the time constants, the pressure in the blood vessels, a cardiovascular compliance and vessel compliance.

19. One or more non-transitory machine readable information storage mediums comprising one or more instructions which when executed by one or more hardware processors causes:
  receiving, by a one or more hardware processors, a plurality of systolic phase parameters and a plurality of diastolic phase parameters associated with a cardiovascular model;
  computing, by the one or more hardware processors, a systolic phase of a PPG signal based on the plurality of systolic phase parameters by utilizing a systolic contractility function and a baroreflex control, wherein the systolic contractility function comprises a plurality of systolic time constants, a systolic duration and a cardiac cycle duration;

computing, by the one or more hardware processors, a diastolic phase of the PPG signal based on a plurality of diastolic phase parameters by utilizing a diastole contractility function and the baroreflex control, wherein the diastolic contractility function comprises a plurality of diastolic time constants, a diastolic duration and the cardiac cycle duration;

generating, by the one or more hardware processors, a synthetic PPG signal based on the computed systolic phase and the diastolic phase of the PPG signal, wherein the synthetic PPG signal is associated with a plurality of the synthetic PPG signal parameters;

simultaneously fetching, by the one or more hardware processors, a plurality of predetermined morphological features associated with a PPG signal from a database;

optimizing, by the one or more hardware processors, the plurality of synthetic PPG signal parameters to obtain a plurality of optimized parameters by utilizing the plurality of predetermined morphological features; and generating, by the one or more hardware processors, the plurality of synthetic PPG signals corresponding to the plurality of disease conditions by varying the plurality of parameters, wherein the plurality of parameters comprises the plurality of optimized parameters and a plurality of cardiovascular model parameters.

* * * * *